United States Patent [19]
Chang et al.

[11] Patent Number: 4,721,704
[45] Date of Patent: Jan. 26, 1988

[54] POTENT SYNTHETIC ATRIAL PEPTIDE ANALOGS

[75] Inventors: Jaw-Kang Chang; Ding Chang, both of San Carlos, Calif.

[73] Assignee: Peninsula Laboratories, Inc., Belmont, Calif.

[21] Appl. No.: 861,528

[22] Filed: May 9, 1986

[51] Int. Cl.$^4$ .......................... A61K 37/24; C07K 7/10
[52] U.S. Cl. .......................................... 514/11; 514/13; 530/326
[58] Field of Search ...................... 530/326; 514/11, 13

[56] References Cited
U.S. PATENT DOCUMENTS

| | | | |
|---|---|---|---|
| 3,766,162 | 10/1973 | Spector | 530/405 |
| 3,817,837 | 6/1974 | Rubenstein et al. | 435/7 |
| 3,998,943 | 12/1976 | Ullman | 570/190 |
| 4,496,544 | 1/1985 | Needleman | 514/13 |
| 4,508,712 | 4/1985 | Needleman | 514/11 |
| 4,557,864 | 12/1985 | Needleman | 530/326 |
| 4,607,023 | 8/1986 | Thibault et al. | 530/326 |

OTHER PUBLICATIONS

Salacinski et al., *Analytical Biochemistry*, 117, pp. 136–146 (1981).
DeBold et al., *Fed. Proc.*, 42(3), Abstract 1870, p. 611 (1983).
Grammer et al., *Biochem. Biophys. Res. Commun.*, 116(2), pp. 696–703 (1983).
Flynn et al., *Biochem. Biophys. Res. Commun.*, 117(3), pp. 859–865 (1983).
Thibault et al., *FEBS Letters*, 167, pp. 352–356 (1984).
Kangawa et al., *Biochem. Biophys. Res. Commun.*, 118(1), pp. 113–139 (1984).
Kanagawa et al., *Biochem. Biophys. Res. Commun.*, 119(3), pp. 933–940 (1984).
Tang et al., *Regulatory Peptides*, 9, pp. 53–59 (1984).

*Primary Examiner*—Delbert R. Phillips
*Attorney, Agent, or Firm*—Majestic, Gallagher, Parsons & Siebert

[57] ABSTRACT

Biologically active atrial peptide analogs having 21 or 22 amino acid residues are provided with potent diuretic and natriuretic activities, and which lower blood pressure. These analogs have a $\beta$-mercaptopropanoic acid derivative moiety at the N-terminus and have D-Alanine at the 3 position of the amino acid sequence.

11 Claims, 4 Drawing Figures

POTENT SYNTHETIC ATRIAL PEPTIDE ANALOGS

FIELD OF THE INVENTION

This invention relates to new synthetic atrial peptides having useful natriuretic, diuretic and antihypertensive activity.

BACKGROUND OF THE INVENTION

Cells of the atrial myocardium in mammals such as rat, dog, cat and human contain numerous membrane-bound storage granules, and resemble those which are in peptide-hormonal producing cells. Various atrial natriuretic peptides having amino acid sequences in the range of from about 19 to 59 amino acid sequences have recently been discovered.

Thus, DeBold et al., *Fed. Proc.* 42(3), Abstract 1870, page 611 (1983), report the purification of an atrial natriuretic peptide having a molecular weight of 5150 daltons and a sequence of 47 amino acids, which the investigators designated "Cardionatrin I".

Grammer et al., *Biochem. Biophys. Res. Commun.* 116(2), 696–703 (1983) discloses the partial purification of a rat atrial natriuretic factor having a molecular weight of approximately 3800 and containing 36 amino acid residues.

Flynn et al., *Biochem Biophys Res. Commun.* 117(3), 859–65 (1983), and Kangawa and Matsuo, *Ibid.*, 118(1), 131–39 (1984), disclose atrial natriuretic peptides of the rat and human, respectively, having sequences of 28 amino acids.

Thibault et al., *FEBS Letters* 167, 352–56 (1984) disclose the purification of an intermediate molecular weight atrial natriuretic peptide having 73 amino acids, and Kangawa et al., *Biochem Biophys. Res. Commun.* 119(3), 933–40 (1984), disclose the purification of an intermediate molecular weight beta-rat atrial natriuretic peptide having 48 amino acids.

Tang et al., *Regulatory Peptides*, 9, pp. 53–59 (1984) describe five peptides, four of which were isolated from rat atria and the fifth from human atria. These peptides were found to possess natriuretic and diuretic activities and to relax vascular and non-vascular smooth muscles. The four peptides isolated from rat atria were named atrial natriuretic factor and atriopeptin I-III, respectively. The fifth, isolated from human atria, was named α-human atrial natriuretic polypeptide (α-hANP). The five peptides contained from 21 to 28 amino acid residues U.S. Pat. Nos. 4,508,712 (issued Apr. 2, 1985) and 4,496,544 (issued Jan. 29, 1985), inventor Needleman, disclose certain atrial peptides said to have natriuretic activity, with peptides disclosed in the former patent having a high molecular weight and those in the later patent having been obtained by fractionation of rat atrial extracts.

SUMMARY OF THE INVENTION

In one aspect of the present invention, novel, synthetic atrial peptide analogs are provided having the following amino acid sequence

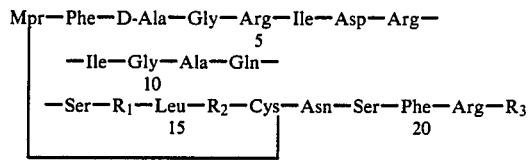

wherein "Mpr" is a β-mercaptopropanoic acid derivative, $R_1$ is Gly or D-Ala, $R_2$ is Gly or D-Ala, and $R_3$ is OH, $NH_2$, Tyr-OH, or Tyr-$NH_2$.

In the above peptide structure, the amino acid residues, or components, are designated by conventional abbreviations and represent the normal "L" stereoisomer, except that "D-Ala" is alanine in the "D", or dextro, form.

The novel atrial peptides of the present invention are analogs of the naturally occurring Atriopeptin III, which has been isolated from rat atria, and the inventive peptides are biologically active. Preferred embodiments have been found to have greater potency, or biological activity, than does Atriopeptin III or α-ANP. A particularly preferred embodiment of the present invention is an atrial peptide analog having the following amino acid sequence and being in the amide form:

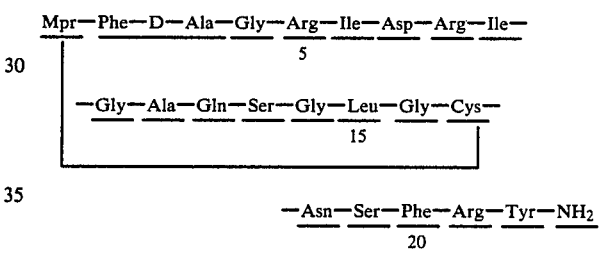

This particularly preferred embodiment increases the cyclic GMP produced in assayed cells at considerably greater levels than does Atriopeptin III, has a much greater hypotensive effect, and is a more potent diuretic. Because the subject peptides are generally more potent than both α-hANP and Atriopeptin III, they are more therapeutically useful than prior art peptides.

DETAILED DESCRIPTION OF THE PREFERRED EMBODIMENTS

Figure 1:
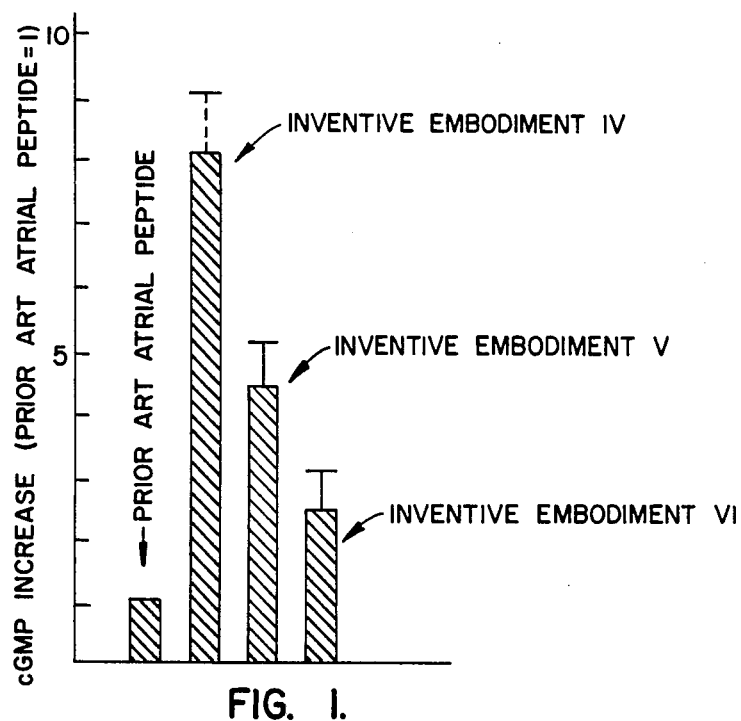
FIG. 1 illustrates the cGMP in lung cells induced by three embodiments of the invention and by Atriopeptin III.

Atriopeptin III and α-hANP have been shown to have about comparable hypotensive, diuretic and natriuretic activities. (Tang, et al., supra.) Atriopeptin III, known to the art and naturally occurring in rat atria, has 24 amino acids in its sequence and has the structure illustrated by Formula I, below.

In the Formula I peptide structure (and in subsequent illustrations or references), the amino acid components are designated by conventional abbreviations as follows:

| Amino Acid | Abbreviated Designation |
|---|---|
| L-Alanine | Ala |
| D-Alanine | D-Ala |
| L-Arginine | Arg |
| L-Aspartic acid | Asp |
| L-Asparagine | Asn |
| L-Cysteine | Cys |
| L-Glutamic acid | Glu |
| L-Glutamine | Gln |
| Glycine | Gly |
| L-Histidine | His |
| L-Isoleucine | Ile |
| L-Leucine | Leu |
| L-Lysine | Lys |
| L-Methionine | Met |
| L-Phenylalanine | Phe |
| L-Proline | Pro |
| L-Serine | Ser |
| L-Threonine | Thr |
| L-Tryptophane | Trp |
| L-Tyrosine | Tyr |
| L-Valine | Val |

As will be discussed hereinafter, embodiments of the invention must have at least one D-Ala residue at a position analogous to a glycine residue of Atriopeptin III.

Embodiments of the present invention are analogous to Atriopeptin III along much of their sequences, but all are des the two serines present at the 1 and 2 positions of Atriopeptin III. Thus the inventive peptides are "shifted" by two positions in numbered sequence with respect to Atriopeptin III. All of the inventive embodiments have a β-mercaptopropanoic acid ("Mpr") derivative aa a peptide-bond linked moiety at the N-Terminal end (rather than the 3 position cysteine of Atriopeptin III), and all have D-Ala at the 3 position (rather than the 5 position Gly of Atriopeptin III). As will be understood, the N-Terminal ends of these analogs do not have a free amino group (such as in cysteine or serine). Nevertheless, use of the conventional terminology "N-Terminal" will be retained throughout this description. Embodiments of the invention are peptides having 21 or 22 amino acids and are illustrated by the Formula II structure, below.

In the Formula II illustration depicted in Table I, Mpr is a β-mercaptopropanoic acid derivative, $R_1$ is Gly or D-Ala, $R_2$ is Gly or D-Ala, and $R_3$ is OH, $NH_2$, Tyr-OH, or Tyr-$NH_2$.

The peptides of Formula II may be readily prepared by solid phase peptide synthesis techniques. The synthesis is commenced from the carboxyl terminal end of the peptide by coupling the appropriate amino acid, i.e., either L-Arginine or L-Tyrosine, to a suitable resin support, such as a p-methyl benzhydrylamine resin, a chloromethylated resin or a hydroxymethyl resin.

The coupling reaction is carried out with the aid of a carboxyl group activating compound, such as Dicyclohexylcarbodiimide, and with the α-amino group of of the amino acid protected with a protecting group, such as t-butyloxycarbonyl (BOC), benzyl(BZL), p-methylbenzyl (MBZL), t-amyloxycarbonyl(AOC), tosyl(TOS), o-bromobenzyloxycarbonyl(BrZ), cyclohexyl (OHEX), or 26-dichlorobenzyl(BzlCl$_2$). Following this coupling reaction, the α-amino protecting group is removed, such as by using trifluoroacetic acid in methylene chloride, trifluoroacetic alone or HCl in dioxane, with the deprotection being carried out at a temperature between about 0° C. and room temperature Thereafter, each succeeding amino acid in the sequence is coupled in the same manner stepwise in the desired order, culminating in the addition of protected Mpr to obtain the peptide of Formula II.

As an alternative to adding each amino acid separately to the reaction, some may be coupled prior to addition to the solid phase reactor. Each protected amino acid or amino acid sequence is introduced into the solid phase reactor in excess (about a three- or four-fold excess), and the coupling may be carried in a medium of dimethylformamide:methylene chloride 1:1, or in dimethylformamide or methylene chloride alone. The success of the coupling reaction at each stage of the synthesis may be monitored by the nihydrin reaction After the final moiety in the sequence, i.e., Mpr has been coupled, the deprotection step is carried out by treatment with a reagent such as hydrogen fluoride. Mpr is available, for example, from Sigma Chemical Company. Prior to coupling it has the structure illustrated by Formula IIIA, below, and following coupling (i.e., the "Mpr derivative" or coupled moiety) has the structure illustrated by Formula IIIB, below.

Formula IIIA

HS CH$_2$CH$_2$COOH

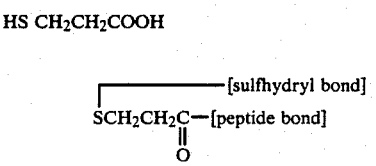

The cleaved peptide is oxidized to form a sulfhydryl bridge between the 1 position Mpr and the 17 position cysteine (Mpr may be viewed as cysteine with the amino group removed).

When a p-methyl benzhydryl amine resin has been used as the resin support, the Formula II peptide cleaved (by treatment with a reagent such as hydrogen fluoride) from the resin will be in the carboxyl terminal amide form. When a chloromethylated resin or a hydroxymethyl resin has been used as the resin support, the peptide cleaved from the resin support will be in the form of the carboxyl terminal benzyl ester, which may then be readily converted by methods well known in the art to provide the carboxyl terminal free acid or amide forms of the peptide of Formula II peptide.

The following examples, methods, materials and results are described for purposes of illustrating the present invention. However, other aspects, advantages and modifications within the scope of the invention will be apparent to those skilled in the art to which the invention pertains.

Example I exemplifies preparation of a particularly preferred embodiment of the present invention, which has the structure illustrated by Formula IV, below, and will sometimes hereinafter be referred to as the "Formula IV embodiment. The Formula IV embodiment is preferably in the amide form (as shown in Table I), but is also quite potent in the free acid form.

EXAMPLE I

Solid Phase Synthesis of the Formula IV Embodiment

The manual synthesis of the Formula IV embodiment was performed in a fritted half-liter glass reaction vessel with agitation and filtration facilitated by a stream of nitrogen at 20 psi.

Boc-Tyr(o-Br-Z)-P-MeBHA (P-Methyl benzylhydrylamine Resin) was used as the solid-support (0.63 meq/g of resin. Total lmM, 1.6g). A solid-phase peptide synthesis protocol of washing, deprotection, neutralization and coupling steps were as follows:

1. Washing with $CH_2Cl_2$ thrice, 1 min.
2. Prewashing with 40% $CF_3COOH$ in $CH_2Cl_2$ (0.05% indole) once, 1 min.
3. Deprotection with 40% $CF_3COOH$ in $CH_2Cl_2$ (0.05% indole) for 30 mins.
4. Washing with $CH_2Cl_2$ once, 1 min.
5. Washing with EtOH once, 1 min.
6. Washing with $CH_2Cl_2$ once, 1 min.
7. Prewashing with 10% $Et_3N$ in $CH_2Cl_2$ once, 1 min.
8. Neutralization with 10% $Et_3N$ in $CH_2Cl_2$ for 10 mins.
9. Washing with $CH_2Cl_2$ thrice, 1 min.
10. Coupling of protected amino acid (3 molar excess) and Dicylohexylcarbodiimide (DCC, 3 molar excess) in $CH_2Cl_2$ and DMF (1:1) for 2 hours.

$CH_2Cl_2$, $CF_3COOH$ and $Et_3N$ were all glass distilled. DMF was distilled from ninhydrin under reduced pressure. EtOH was anhydrous reagent grade.

The synthesis cycle was continued by incorporating the corresponding protected amino acid sequentially from the C-terminal until the successful coupling of the Mpr(MBZl) residue. When coupling L-glutamine or L-asparagine 1-hydroxybenzotriazole is to be added with DCC (coupling agent) and DNF as solvent. The Boc-amino acids incorporated were functionally protected: Boc-Ser(Bzl); Boc-Arg(Tos); Boc-Cys(MBzl) and Boc-Asp(OcHex). All amino acids (except of course Gly and the D-Ala, which was added as the twentieth amino acid, and the second from Mpr) were of the L-configuration.

Double couplings or acetylations were carried out as deemed necessary by the Kaiser ninhydrin test.

The protected peptide resin thus obtained (1 mM/4.5g of dried resin) was treated with anhydrous HF (10 ml/g or resin) in the presence of distilled anisole (1.5 ml/g of resin) and $Me_2S$ (0.25 ml/g of resin) at 0° C. for one hour. The cleaved linear form of the peptide was precipitated in anhydrous ether and extracted with aqueous acetic acid (50%) and then diluted with distilled water (10 liters).

It was oxidized to form the disulfide bridge between Mpr and the 17 position cysteine by the addition of 0.01M $K_3Fe(CN)_6$ dropwisely at pH 7.5 (pH was adjusted by addition of $NH_4OH$ solution). With the persistence of a yellow color in the solution for 30 min., the solution was acidified with HOAc to pH 4 to 4.5. Absorption of the peptide from the solution was performed by addition and overnight stirring of Bio-Rex 70 cation exchange resin (H+ form, 150 g, available from Bio-Rad Laboratories). This resin was filtered, column-packed and eluted with 70% of acetic acid to give the cyclized crude peptide (0.8 g).

This crude sulfhydryl-free peptide (negative test with nitroprusside reagent) was purified on a chromatography C-18 column (3×27 cm, 40 microns) at a 2.5 ml/min. flow rate using a 0–50%B linear gradient. Buffer A: 0.05M $NH_4OAc$, pH 4.0, 1 liter; Buffer B: 60% $Ch_3CH$ in Buffer A, 1 liter. The eluent was monitored by UV at 278 nm and analyzed by thin-layer chromatography and analytical HPLC, which should afford a pure product (73 mg).

Analytical thin-layer chromatography was performed by spotting 50 microgram of peptide on a silica gel plate (10×20 cm) and developed in BuOH:phyridine:water:HOAc 6:6:4.8:1.2 with ninhydrin detection.

Analytical HPLC was performed by the injection of 30 microgram/25 microliter of Buffer A (Buffer A, water:$CF_3COOH$/99.9:0.1) of peptide on a vydac C-18 analytical column (4.6×250 mm, 300A pore size, 5 micron dp) at a 1 ml/min. flow rate and 2.5% Buffer B/min. gradient elution. The eluent was monitored by UY at 215 nm and 0.5 AUFS attenuation at a 2 mm/min. chart speed. Buffer B, $CH_3CN$:$H_2O$:TFA (60:39.9:0.1). Analytical HPLC was augmented by the use of a second buffer system (Buffer A and Buffer B).

Purity of the Formula IV embodiment was determined by analytical thin-layer chromatography, Electrophoresis and high pressure liquid chromatography. Amino acid analysis was performed on a Beckman amino acid analyzer model 119CL after the peptide was subjected to acid hydrolysis in 6N HCl for 24 hours at 110° C. Purity of the synthetic Formula IV embodiment was 90% or better based on the HPLC analysis.

Higher purity peptides can be obtained by using preparative HPLC.

| Electrophoresis: Whatman 3 MM Pyr:acet. buffer, pH 3.5; 1500 V., 1 hr. Results: Single spot $R_f$ = 0.47 with reference to arginine. AMINO ACID ANALYSIS: | | |
|---|---|---|
| | Theory | Found |
| $NH_3$ | 3 | 2.75 |
| Arg | 3 | 2.93 |
| Asp | 2 | 1.92 |
| Ser | 2 | 1.81 |
| Glu | 1 | 1.01 |
| Gly | 4 | 4.10 |
| Ala | 2 | 2.04 |
| CysH | 1 | 0.34* |
| Ile | 2 | 1.87 |
| Leu | 1 | 1.07 |
| Tyr | 1 | 1.01 |
| Phe | 2 | 2.00 |
| Mpr | 1 | ...** |

*Cys is destroyed during acid hydrolysis
**Mpr is not detected by AAA

EXAMPLE II

By solid phase syntheses analagous to preparation of the Formula IV embodiment, several embodiments in accordance with the present invention were likewise prepared having the structures illustrated by Formulas V and VI, below (hereinafter sometimes referred to as the Formula V embodiment and the Formula VI embodiment, respectively), which preferably are in the amide form as shown.

In addition to the specifically illustrated Formula IV, V and VI embodiments, several closely related analogs thereto within the scope of the invention have the structures and are illustrated as Formulas VII and VIII, below. These can also be in the acid or amide form at the C-terminus, but preferably are in the amide form as shown. Formulas I, II and IV through VIII are set forth in Table I, below, and have the Mpr and amino acid sequence numbers included for convenience.

TABLE I

Formula I
*(Prior Art Atriopeptin III)*

Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr
1   2   3   4   5   6   7   8   9   10  11  12  13  14  15  16  17  18  19  20  21  22  23  24

Formula II
*(Inventive Peptides)*

Mpr-Phe-D-Ala-Gly-Arg-Ile-Asp-Arg-Ile-Gly-Ala-Gln-Ser-$R_1$-Leu-$R_2$-Cys-Asn-Ser-Phe-Arg-$R_2$
1   2   3     4   5   6   7   8   9   10  11  12  13  14  15  16  17  18  19  20  21  22

Formula IV
*(Preferred Embodiment)*

Mpr-Phe-D-Ala-Gly-Arg-Ile-Asp-Arg-Ile-Gly-Ala-Gln-Ser-Gly-Leu-Gly-Cys-Asn-Ser-Phe-Arg-Tyr-NH$_2$
1   2   3     4   5   6   7   8   9   10  11  12  13  14  15  16  17  18  19  20  21  22

Formula V
*(Preferred Embodiment)*

Mpr-Phe-D-Ala-Gly-Arg-Ile-Asp-Arg-Ile-Gly-Ala-Gln-Ser-Gly-Leu-D-Ala-Cys-Asn-Ser-Phe-Arg-NH$_2$
1   2   3     4   5   6   7   8   9   10  11  12  13  14  15  16    17  18  19  20  21

Formula VI
*(Preferred Embodiment)*

Mpr-Phe-D-Ala-Gly-Arg-Ile-Asp-Arg-Ile-Gly-Ala-Gln-Ser-D-Ala-Leu-Gly-Cys-Asn-Ser-Phe-Arg-NH$_2$
1   2   3     4   5   6   7   8   9   10  11  12  13  14    15  16  17  18  19  20  21

Formula VII
*(Preferred Embodiment)*

Mpr-Phe-D-Ala-Gly-Arg-Ile-Asp-Arg-Ile-Gly-Ala-Gln-Ser-Gly-Leu-D-Ala-Cys-Asn-Ser-Phe-Arg-Tyr-NH$_2$
1   2   3     4   5   6   7   8   9   10  11  12  13  14  15  16    17  18  19  20  21  22

Formula VIII
*(Preferred Embodiment)*

Mpr-Phe-D-Ala-Gly-Arg-Ile-Asp-Arg-Ile-Gly-Ala-Gln-Ser-D-Ala-Leu-Gly-Cys-Asn-Ser-Phe-Arg-Tyr-NH$_2$
1   2   3     4   5   6   7   8   9   10  11  12  13  14    15  16  17  18  19  20  21  22

The inventive peptides are biologically active, as are shown by various in vitro and/or in vivo assays and tests. For example, the inventive embodiments demonstrate the capacity to induce cyclic GMP production in cells.

Cyclic guanosine monophosphate (cyclic GMP) is a cyclic nucleotide that is present in animal cells, although at concentrations much lower than cyclic AMP. Cyclic GMP levels increase during responses of intact cells to various signaling ligands. One function of cyclic GMP may be to modulate responses initiated by an increase in the concentration of free intracellular $Ca^{2+}$. Cyclic GMP acts primarily by activating certain protein kinases, which broadly function as activators or modulators of other cellular proteins.

EXAMPLE III

Cyclic GMP Assay

Several embodiments of the present invention (e.g., inventive embodiments IV, V and VI) were tested with rat lung tissue and, for comparison, Atriopeptin III, to determine the amount of cyclic guanosine 3', 5'-monophosphate (cyclic GMP). The assays measure the ability of the test peptides to bind to the cell membrane receptor of intact rat lung cells and selectively stimulate production of cyclic GMP, as does Atriopeptin III itself.

Male and female Wistar rats weighing 230-250 g were sacrificed by decapitation. Samples of fresh lung tissue (10-20 mg) of the rats were incubated with either Atriopeptin III, inventive embodiment IV, V or VI in varying concentrations ($10^{-9}$ to $10^{-7}$ M) at 37° C. for 10 min. in the medium of Kerb's solution saturated with 95% $O_2$ and 5% $CO_2$. The medium was aspirated. The tissue was homogenized at 3,000 rpm for 2 min. in 1.5 ml of trichloroacetic acid with a motor-driven Teflon pestle and then centrifuged at 1,000 xg for 10 min. The supernatents were mixed with 3 ml water saturated ether to remove the trichloroacetic acid. A 1 ml aliquot of each sample with then lyophilized and redissolved in 1 ml buffer. 100 ml of each sample was used to determine amount of cyclic GMP by radioimmunoassay.

FIG. 1 shows that inventive embodiments IV, V and VI at $10^{-8}$M increased the cyclic GMP content by about 8, 4.5 and 2.2 times, respectively, with respect to Atriopeptin III at $10^{-8}$ M, and thus are considerably more potent than Atriopeptin III. At a dose of $10^{-7}$ M, the cyclic GMP content was increased about 2.1 fold by Atriopeptin III and about 2.6 fold by inventive embodiment IV.

A number of heart disease and hypotension patients have recently been found to be therapeutically aided by administration of α-hANP in 400 μg bolus doses, with α-hANP decreasing blood pressure and acting as a diuretic. Some researchers believe that the content of α-hANP in the plasma of patients with heart failure diseases may be less than in the plasma of normal persons, which indicates that the edema and uropenia in heart failure disease may be caused by diminished rates of α-hANP secretions by the atrium. Thus, for example, in four patients with serious edema and uropenia induced by heart failure, the concentration of α-hANp-like immunoreactivity was found to be less than 10.0 pmol/L or undetectable, wherein normal human plasma has a concentration of about 28.8 pmol/L.

Examples IV and V, below, illustrate the blood pressure lowering and diuretic properties of a preferred embodiment of the invention. In the therapeutic use of the inventive peptides in treating heart disease and hypertensive patients, effective amounts may be administered for decreasing blood pressure and/or for natriuretic and diuretic activity. Preferred amounts administered are in from about 100–400 μg doses, preferably administered by I.V. bolus. Depending upon the mode of administration, the inventive atrial peptide analog may be formulated with a wide variety of physiologically acceptable carriers, such as aqueous saline and phosphate buffered saline, and may include physiologically acceptable excipients.

EXAMPLE IV

The diuretic effect of inventive embodiment IV and of Atriopeptin III for comparison, was determined as follows.

Male and female Wistar rats, weighing 230-250 g, were used in the experiments. Measurements of urine flow were made in animals that were first intubated with normal saline, 3-5 ml per 100 g body weight. Assays were conducted on animals anesthetized with urethane, 1 g/kg, i.p. After litigation of the penis, urine was collected directly from a cannula inserted into the bladder every 2.0 minutes. Blood pressure was measured via a cannula inserted into the left carotid artery and attached to a pressure transducer and recorder. Peptides, dissolved in sterile saline, were injected into a cannulated femoral vein.

Figure 2:
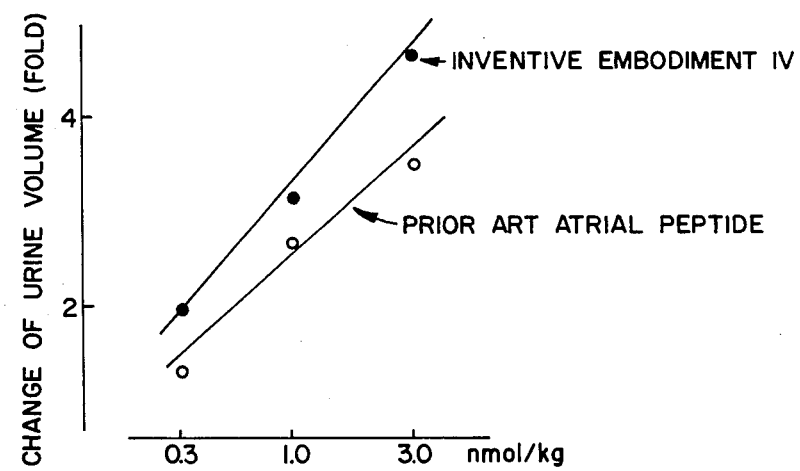
FIG. 2 plots the diuretic time course for animals having receiving either an embodiment of the invention or Atriopeptin III.

FIG. 2 plots the data of the determinations. The results show that the diuretic time course of inventive embodiment IV is simlar to that of Atriopeptin III, but that the peak effect of inventive embodiment IV is more powerful. At doses of 0.3, 1 and 3 nmol/kg, the effect of inventive embodiment IV was 2.7, 2.6 and 4 times respectively more potent than that of Atriopeptin III.

EXAMPLE V

Dose-dependent responses showing the depressor action (that is, lowering blood pressure) for inventive embodiment IV and, for comparison, Atriopeptin III, were conducted on the rats described in Example IV.

Figure 3:
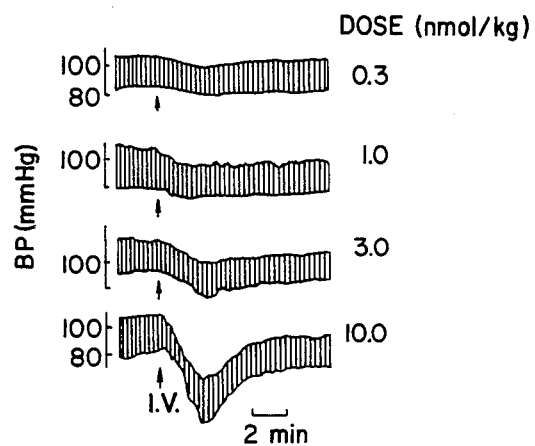
FIG. 3 plots a dose-response depressor effect of animals' blood pressure after receiving a dose of an embodiment of the invention.

A catheter was placed in the left carotid artery and attached to a pressure transducer and recorder to measure the mean arterial pressure (MAP) of the rats anesthetized with urethane. Atriopeptin III and inventive embodiment IV were respectively dissolved in 0.1 ml of sterile normal saline and injected in bolus into a cannulated femerol vein. Dose response was observed in the same animals given multiple injections at 1.5 hr. intervals when the basal level of MAP could be resumed. The loss of body fluid in the rats was compensated by a continuous infusion of normal saline (0.5 ml/hr) into the vein with a peristaltic pump. FIG. 3 illustrates the data for the Formula IV embodiment.

Figure 4:
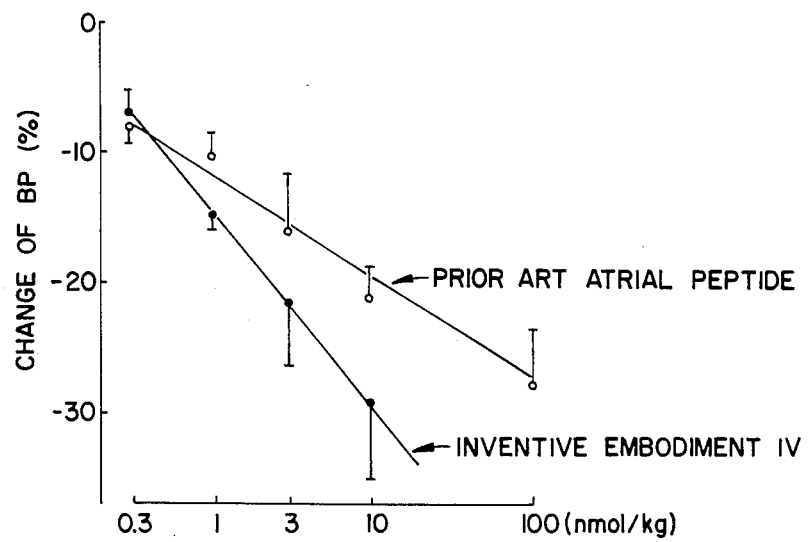
FIG. 4 plots the hypotensive effect in animals three minutes after I.v. administration of either an embodiment of the invention or of Atriopeptin III.

It was found that inventive embodiment IV possesses a more potent peak depressor effect that does Atriopeptin III. Thus, for example, FIG. 4 is a comparison of the hypotensive effect between inventive embodiment IV for one group and Atriopeptin III for another group (3 min. after I.V. administration to 6-8 rats per group). The result shows that at doses of 1.3 or 10 mol/kg, the effects of inventive embodiment IV are up to 10 times more potent than the effects of Atriopeptin III.

Compounds of the subject invention may also be used for preparing antiserum for use in immunoassays employing labeled peptides and for diagnostic uses, such as competitive immunoassays. The inventive embodiments may also be immobilized by means known to the art to solid supports, such as agarose, glass or polyacrylamide, for various diagnostic separations and applications such as affinity chromatography. When coupling the inventive peptides, they are preferably in the free acid form.

Inventive embodiment IV, for example, binds as well as α-ANP to antiserum, and thus can be used to inhibit binding of $^{125}I$-α-hANP. The peptides may be conveniently conjugated to antigen by conventional means, and may be labeled with a variety of labels which are conventionally employed in the literature. Illustrative labels are radioactive tags, such as $^{125}I$ or $^3H$, enzymes, fluorescers, or the like. For example, U.S. Pat. Nos. 3,766,162, 3,817,837 and 3,998,943 describe labeling and immunoassay, and are incorporated herein by reference.

It is believed that compounds of the subject invention may be more potent than α-hANP and Atriopeptin III due to an increased chemical stability and thus are more resistant to enzyme degradation. This may be due to the fact that there is no attackable amino group on Mpr, as there is on the cysteine at the 3 position of Atriopeptin III or at the 7 position of α-hANP. The inventive peptides also have changed conformations with respect to α-hANP and Atriopeptin III. Although the amide form, rather than the acid form, is usually preferred for the inventive analogs, the potency of inventive embodiment IV in acid form, for example, is still considerably better than Atriopeptin III.

It is believed that degradative enzyme resistance (and potency) is also conveyed to the inventive peptides of Formula II by means of the D-Ala acid residue at the 3 position thereof, and to some extent also by a D-Ala presence at the 16 and/or 14 positions in some of the embodiments. Preparation of antiserum to the Formula II peptides and radiolabeling are illustrated by Example VI, below.

EXAMPLE VI

Goat anti-rabbit immunoglobulins and horseradish/anti-horseradish peroxidase are available from DAKO (Copenhagen, Denmark). Thyroglobulin and other chemicals are available from Sigma Company (St. Louis).

A Formula II peptide (5 mg) and thyroglobulin 25 mg may be dissolved in 1 ml (pH 7.4) 0.2M phosphate buffer. To this solution, 10 μl of 5% glutaraldehyde may be added. The solution may be kept at room temperature for 40 min. The peptide-thyroglobulin conjugate may be dialyzed against $H_2O$ and then lyophilized. The conjugate may be dissolved in saline and then emulsified in complete Freund's adjuvant 1 ml emulsion containing 1 mg peptide-thyroglobulin conjugate may be injected subcutaneously into the back of rabbits. For the subsequent immunization, 500 μg antigen emulsified in complete Freund's adjuvant is injected. The immunization is repeated every 2 or 4 weeks, and at 3 months after the first injection the rabbit is bled.

The Formula II peptide may be labeled with $^{125}I$ by the Iodogen method. Salacinski, P. R. F., McLean C., Sykes, V. V. and Lpwry, P. J., "Iodination of Proteins, Glycoproteins and Peptides Using a Solid Phase Oxidizing Agent, 1,3,4,6-tetrachloro-3,6-diphenyl glycouril (Iodogen)," *Analytical Biochemistry*, 117, 136–146 (1981). To a prelyophilized Iodogen tube containing 20 μg of Iodogen, 1 nmol peptides in 40 μl of 0.1M sodium phosphate buffer (pH 7.4) and 0.5 mCi Na $^{125}I$ (2.5 μl) is added. After 4 min. of mixing by vortex, the iodinated peptides are then purified with Sephadex G10 (2.0×10 cm, available from Pharmacia Fine Chemicals), column chromatography eluted with 50% $CH_3COOH$ and purified by HPLC using the TFA (trifluoracetic assay) system.

Although various aspects of the present invention have been described with respect to a preferred embodiment thereof, it will be understood that the invention is entitled to protection within the full scope of the appended claims.

We claim:

1. An atrial peptide analog having the structure

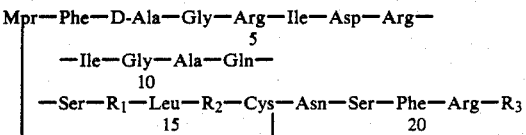

wherein Mpr is a β-mercaptopropanoic acid derivative, $R_1$ is Gly or D-Ala, $R_2$ is Gly or D-Ala, and $R_3$ is OH, $NH_2$, Tyr-OH, or Tyr-$NH_2$.

2. The atrial peptide analog as in claim 1 wherein $R_1$ and $R_2$ are Gly.

3. The atrial peptide analog as in claim 2 wherein $R_3$ is Tyr-OH or Tyr-$NH_2$.

4. The atrial peptide analog as in claim 2 wherein $R_3$ is Tyr-$NH_2$.

5. The atrial peptide analog as in claim 1 wherein one of $R_1$ and $R_2$ is Gly and the other of $R_1$ and $R_2$ is D-Ala.

6. The atrial peptide analog as in claim 5 wherein $R_3$ is $NH_2$ or Tyr-$NH_2$.

7. A therapeutic composition for producing diuresis, natriuresis, or for lowering blood pressure comprising a therapeutically effective amount of the atrial peptide analog of claim 1.

8. A method for producing diuresis, natriuresis or for lowering blood pressure in a mammal comprising administering to said mammal a therapeutically effective amount of the peptide analog of claim 1.

9. The method as in claim 8 wherein the therapeutically effective amount is from about 100 μg to about 400 μg and is administered by I.V. bolus.

10. A method for the treatment of edema or hypertension which comprises administering to a mammal afflicted with edema or hypertension an effective amount of a peptide having the formula

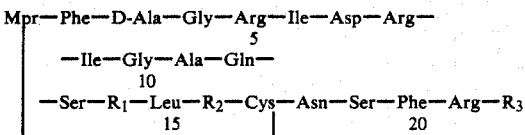

wherein Mpr is moiety having the structure

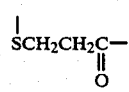

and $R_1$ is Gly or D-Ala, $R_2$ is Gly or D-Ala, and $R_3$ is OH, $NH_2$, Tyr-OH or Tyr-$NH_2$.

11. The method as in claim 10 wherein the peptide is formulated with a physiologically acceptable carrier.

* * * * *

UNITED STATES PATENT AND TRADEMARK OFFICE
CERTIFICATE OF CORRECTION

PATENT NO. : 4,721,704

DATED : Jan. 26, 1988

INVENTOR(S) : Jaw-Kang Chang, et al.

It is certified that error appears in the above-identified patent and that said Letters Patent is hereby corrected as shown below:

Col. 4, line 30:   insert --Formula IIIB--;

Col. 7, Formula II:  at position 22, replace "$R_2$" with --$R_3$--;

Col. 12, line 42:  replace "effect:ve" with --effective--.

Signed and Sealed this

Twenty-fourth Day of May, 1988

Attest:

DONALD J. QUIGG

*Attesting Officer*       *Commissioner of Patents and Trademarks*